United States Patent [19]

Mateson

[11] Patent Number: 5,668,103
[45] Date of Patent: Sep. 16, 1997

[54] AIR CLEANER COMPOSITION

[76] Inventor: Mark Mateson, 905 Berkeley Rd., Wilmington, Del. 19087

[21] Appl. No.: 534,191

[22] Filed: Sep. 26, 1995

Related U.S. Application Data

[63] Continuation of Ser. No. 276,982, Jul. 19, 1994, abandoned.

[51] Int. Cl.$^6$ ........................................................ A61K 7/46
[52] U.S. Cl. .............................. 512/4; 424/76.4; 510/105
[58] Field of Search .......................... 512/3, 4; 424/76.4; 252/174.11

[56] References Cited

U.S. PATENT DOCUMENTS 2,889,254  6/1959  Fiore et al. .................................. 512/3
3,772,215  11/1973  Gould et al. ................................. 512/4
4,067,824  1/1978  Teng et al. ................................. 424/76.4

FOREIGN PATENT DOCUMENTS 2399239  4/1979  France ......................................... 512/4
2452920  12/1980  France ......................................... 512/4
63-135177  6/1988  Japan .......................................... 512/4

*Primary Examiner*—James H. Reamer
*Attorney, Agent, or Firm*—Eugene E. Renz, Jr., P.C.

[57] ABSTRACT

An air cleaner composition comprising a fragranced material and water formed into a solid material by add mixing a solid soap in an amount sufficient to produce a solid having a melting point of at least 110° F.

2 Claims, No Drawings

AIR CLEANER COMPOSITION

This is a continuation application Ser. No. 08/276,982 filed on Jul. 19, 1994, now abandoned.

FIELD OF THE INVENTION

This invention relates to an air cleaner composition. More particularly, the invention relates to a composition useful for eliminating unwanted or undesirable odors in confined areas such as rooms, vehicles and the like.

BACKGROUND OF THE INVENTION

Indoor air pollution is an ever increasing problem. Recent studies by the Environmental Protection Agency indicates that humans are exposed to air pollutants indoors at levels which may be from 2 to 5 times to as much as one hundred times higher than outdoor levels. Since many people spend as much as 90% of their time indoors, this is a particular concern.

Increase in air pollution indoors is due at least in part to modern construction of more tightly sealed buildings and reduced ventilation in order to save energy. The use of synthetic materials for buildings and furnishings has further contributed to the increase in indoor air pollutants.

Of course, the most effective treatment to clean air is to remove the source of the pollutant. A second treatment is to improve the ventilation in the area, assuming clean outside air is available to reduce or remove polluted air. A third treatment method is an air cleaner. A number of air cleaners are on the market presently. These products not only add fragrants to the air, but also add air pollution. Air fresheners of conventional commercial formulations cover up the odor with a more powerful smell. Sometimes, these air fresheners include materials which block the nose from smelling anything. Offending gases are not removed from the air.

There are thousands of identified gases and particulants that pollute the air we breathe. Some of these include smoking odors, pet odors and odors from bathrooms and kitchen, musty smells, housecleaning products, pesticides, personal care products, kerosene and wood stoves. Industrial and automotive emission of gases also cause pollution.

There are presently four methods of cleaning the air which are available on the market. These include mechanical filters, electronic air cleaners, ion generators and chemical air cleaners. Mechanical filters can, of course, be installed in air ducts near the furnace and/or air conditioning units. Alternatively, they may be portable units which force air through a filter. This is suitable for removing large particles, but generally has little effect on odors.

Electronic air cleaners use an electrical field to trap charged particles. Again, they may be pan of a HVAC system or maybe a separate portable unit. Electronic air cleaners are typically electrostatic precipitators in which particles are collected on a series of flat plates. This equipment can remove some odors and particles from the air, although effectiveness varies. There is some concern by medical experts that the charged particles that are created during electronic air cleaning may become air borne and enter human lungs. Some have said that charged particles may be carcinogenic.

Ion generators also use static charges to remove particles and gasses from the air and are located in portable units. Many of these units produce ozone, the gas which charges the particles. Again, particles may be deposited on lungs and could be dangerous while not really removing a large percentage of the particles in the room.

The remaining method, chemical air cleaning, operates by attracting positive ions to the chemical which absorbs and takes out the air borne pollutants and other gasses. It is believed by some medical experts to be safer than electronic or ion generating units.

One chemical composition which is useful for air freshening is described in GRIMSHAW, et al U.S. Pat. No. 4,663,081. GRIMSHAW, et al disclosed a liquid composition for freshening air via a wick which supplies a liquid to a surface. The liquid contains twenty to seventy percent water and eight to thirty percent perfume. GRIMSHAW, et al discloses that certain solid compositions having water up to about four percent by weight.

DUMAS, U.S. Pat. No. 4,810,690 describes a non-flammable air freshener using forty to sixty-five percent of organic solvent and fifteen to fifty percent of water. Again, this is a liquid wick evaporator and concern is expressed for premature blocking of the wick.

Finally, DICKERSON, et al, U.S. Pat. No. 5,047,234, describes and air freshener composition of the aqueous type in which the formulation remains liquid. Inorganic metal salts are taught as being effective to enhance emulsion stability for these liquid positions.

At the present time, none of the air cleaner compositions previously known are completely successful in removing pollutants from the air. Accordingly, it is an object of this invention to provide an improved formulation for an air cleaner composition.

Another object of this invention is to provide a solid air cleaner composition.

Yet another object of this invention is to provide an air cleaner composition which comprises at least 70 percent by weight water based on the total weight.

Other objects will appear hereinafter.

SUMMARY OF THE INVENTION

It has now been discovered that the above and other objects of the present invention may be accomplished in the following manner. Specifically, an improved air cleaner composition has been discovered. The composition of this invention comprises a fragrance material and water which are mixed and then formed into a solid material by add mixing solid soaps in an amount sufficient to produce a solid material having a melting point of at least 110° F.

In the preferred embodiment, the amount of water comprises at least 70 percent by weight of the total weight. The composition will contain at least 20 percent by weight, based on the total weight of solids after evaporation of the fragranced material and substantially all of the water.

In a preferred embodiment, the device includes from about 0.1 to about 10 percent by weight of a alcohol such as monohydric alcohols having 2 to about 12 carbon atoms. The preferred embodiment also includes a polymeric binder for the solid material.

While a variety of fragrances may be employed in the present invention, all that is necessary for the fragrance is that it be capable of being carried by the water as the water evaporates into the air. The preferred embodiment of the present invention employs a honey abstract as a fragrance.

DETAILED DESCRIPTION OF THE PREFERRED EMBODIMENT

As stated above, the present invention comprises air cleaner composition having a fragranced material and water formed into a solid material by add mixing solid soaps in an amount sufficient to produce a solid having a melting point of at least 110° F.

The soaps of the present invention are any of the conventional soaps which are formed by the reaction of alkali on fat or fatty acids. Soaps of the present invention consist of primarily of sodium and/or potassium salts of these acids. Soaps may generically be defined for the purposes of this invention that class of solid materials typified by as a salt of a fatty acid and a metal.

Of these fatty acid salts or soaps, sodium stearate is most preferred. Preferred formulations include between five and ten percent by weight of sodium stearate. Similarly, soaps formed from oleanthic acids, either as a salt or as an ether, are also preferred.

As stated above, the air cleaner composition of the present invention comprises of a fragrance and water formed into the solid material by mixing with the soap. Preferably, the amount of water ranges from at least sixty percent up to about eighty percent by weight, based upon the total weight. A preferred amount is about seventy percent by weight. The amount of fragrance will depend in part upon the volatile of the other fragrances employed by the room preferably range from about 0.1 to about 3.0 percent by weight. Preferably, about 0.8 to 1.0 percent by weight of the fragrance is satisfactory. The preferred fragrance is a honey abstract commercially available under the trade name CERONAL, manufactured by GIVAUDON-ROURE CORPORATION.

In some instances, it is desirable and even preferred to include a quantity of a monohydric alcohol having 2 to about 12 carbon atoms. Ethanol and isopropanol are preferred alcohols. The amount of alcohol may range from as low as one percent to as much as ten percent by weight. Preferred amounts range from about eight percent to about ten percent per weight.

In formulating the air cleaner composition of the present invention, it is sometime useful to include other components. Preferred is the use of a polymeric binder such as, in a preferred embodiment, polyethylene oxide in minor amounts of less than one percent by weight. Other ingredients include surfactants or synthetic soaps. Antifoams such as silicone emulsions are also useful in stabilizing the product during manufacture.

Presented below in Table I is the preferred composition of the present invention. In preparing the composition, which is, of course a solid, the components were mixed under mild mixing conditions until the entire composition formed into a solid. The solid, which melts at least at 110° F, can then be processed into particular sizes and shapes useful for air cleaning composition for various locations. The composition shown in Table I has a melting point of approximately 120° F.

TABLE I

Preferred Composition
(by weight, based upon total weight)

| COMPONENTS | PARTS, BY WEIGHT |
| --- | --- |
| Fragrance | 0.90 |
| Water | 70.97 |
| Sodium Stearate | 7.48 |
| Isopropanol | 8.60 |
| Oleanthic Ether | 0.45 |
| Surfactant | 5.10 |

TABLE I-continued

Preferred Composition
(by weight, based upon total weight)

| COMPONENTS | PARTS, BY WEIGHT |
| --- | --- |
| Propylene Glycol | 4.53 |
| Polyethylene Oxide | 0.34 |
| Triethyl Phosphate | 0.56 |
| Silicone Emulsion | 0.34 |
| 1,5 pentanedial | 0.68 |
| | 99.95 |

In order to demonstrate the efficacy of the present invention, a sample of the composition described in Table I was placed in a variety of environments and was subjective to various odors. Presented below in Table II are twelve experiments in various environments and in the presence of various odors. All of the odors were eliminated.

ENVIRONMENTAL EVALUATION OF ODOR ELIMINATION

TABLE II

| Experiment | Environment | Odor |
| --- | --- | --- |
| 1. | truck cab | cigar smoke |
| 2. | bedroom | musty odor |
| 3. | basement | dog odors |
| 4. | hotel room | vomit |
| 5. | automobile | cigarette |
| 6. | home | cooking odors |
| 7. | computer room | cigar smoke |
| 8. | cat liter box | cat odors |
| 9. | storage area | mildew |
| 10. | home | cigarette |
| 11. | bedroom | dust and mold |
| 12. | apartment | cigarette |

In each instance set forth in Table II above, impartial individuals tested the product of this invention in the environment shown. Without exception, the offending odor was eliminated to the satisfaction of the individual.

Even though particular embodiments of the present invention have been illustrated and described herein, it is not intended to limit the invention and changes and modifications may be made therein within the scope of the following claims.

What is claimed is:

1. A composition having a fragranced material, comprising:

about 0.9 parts of a fragranced material and about 70 parts water formed into a solid material by add mixing about 7.5 parts of sodium stearate, about 8.6 parts of isopropanol, 4.5 parts of propylene glycol and about 0.34 parts of polyethylene oxide and about 0.45 parts of oleanthic ether, to produce a solid having at least seventy percent by weight water, based upon the total weight, and having a melting point of about 120° F., said composition having at least twenty percent by weight of solids after evaporation of said fragranced material and substantially all of said water.

2. The composition of claim 1 wherein said fragranced material is a honey abstract.

* * * * *